US 6,617,127 B2

(12) United States Patent
Quaedflieg et al.

(10) Patent No.: US 6,617,127 B2
(45) Date of Patent: Sep. 9, 2003

(54) SYNTHESIS AND RECOVERY OF ASPARTAME INVOLVING ENZYMATIC DEFORMYLATION STEP

(75) Inventors: Peter J. L. M. Quaedflieg, Geleen (NL); Theodorus Sonke, Guttecoven (NL); Adolf F. V. Wagner, Ludwigsburg (DE)

(73) Assignee: Holland Sweetener Company, V.O.F., Geleen (NL)

( * ) Notice: Subject to any disclaimer, the term of this patent is extended or adjusted under 35 U.S.C. 154(b) by 0 days.

(21) Appl. No.: 09/886,476

(22) Filed: Jun. 22, 2001

(65) Prior Publication Data

US 2002/0025549 A1 Feb. 28, 2002

Related U.S. Application Data

(63) Continuation of application No. PCT/NL99/00787, filed on Dec. 20, 1999.
(60) Provisional application No. 60/119,077, filed on Feb. 8, 1999.

(30) Foreign Application Priority Data

Dec. 22, 1998 (EP) .............................. 98204373

(51) Int. Cl.⁷ .......................... C12P 21/06; C12P 13/22; C12P 21/02; C12N 9/78; C12N 9/80
(52) U.S. Cl. ...................... 435/68.1; 435/108; 435/109; 435/129; 435/227; 435/228
(58) Field of Search ............... 435/68.1, 108, 435/109, 227, 228, 129

(56) References Cited

U.S. PATENT DOCUMENTS

| 4,438,201 A | 3/1984 | Kubo et al. |
| 4,668,625 A | 5/1987 | Cambiaghi et al. |
| 4,745,067 A | 5/1988 | Umezawa et al. |
| 5,834,243 A | 11/1998 | Bogosian |

FOREIGN PATENT DOCUMENTS

| EP | 0149594 | 7/1985 |
| WO | 9602630 | 2/1996 |
| WO | 9803664 | 1/1998 |

OTHER PUBLICATIONS

Rajagopalan et al., "Purification, characterization, and inhibition of peptide deformylase from *Escherichia coli*", Biochemestry, vol. 36, 1997, pp 13910–13918.

Primary Examiner—Herbert J. Lilling
(74) Attorney, Agent, or Firm—Pillsbury Winthrop LLP

(57) ABSTRACT

The invention relates to the synthesis of aspartame involving enzymatic deformylation of an N-formyl-α-L-aspartyl-L-phenylalanine compound by treatment with an enzyme having formylmethionyl peptide deformylase activity and having as a co-factor group 5 to 11 bivalent metal ions. The invention also relates to selective preparation and recovery of aspartame from a mixture of N-formyl-α- and β-L-aspartyl-L-phenylalanine compounds by treatment with such enzyme. And finally, the invention relates to one-pot enzymatic synthesis of aspartame from N-formyl-L-aspartic acid and L- or D,L-phenylalanine methyl ester involving an enzymatic deformylation reaction simultaneously with an enzymatic coupling reaction, as well as to one-pot di- or oligopeptide synthesis by simultaneous enzymatic coupling and deformylation reactions in general.

31 Claims, No Drawings

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      motif

<400> SEQUENCE: 1

Glu Gly Cys Leu Ser
 1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      motif
<220> FEATURE:
<221> NAME/KEY: MOD_RES
<222> LOCATION: (2)
<223> OTHER INFORMATION: Any natural amino acid
<220> FEATURE:
<221> NAME/KEY: MOD_RES
<222> LOCATION: (4)
<223> OTHER INFORMATION: Any natural amino acid
<220> FEATURE:
<221> NAME/KEY: MOD_RES
<222> LOCATION: (7)
```

-continued

```
<223> OTHER INFORMATION: Any natural amino acid

<400> SEQUENCE: 2

Gly Xaa Gly Xaa Ala Ala Xaa Gln
 1               5
```

SYNTHESIS AND RECOVERY OF ASPARTAME INVOLVING ENZYMATIC DEFORMYLATION STEP

This is a Continuation Application of International Application No. PCT/NL99/00787 filed Dec. 20, 1999 which designated the U.S. This application claims the benefit of U.S. Provisional Application No. 60/119,077, filed Feb. 8, 1999.

The invention relates to a method for synthesis of α-L-aspartyl-L-phenylalanine methyl ester (α-APM; aspartame) involving enzymatic deformylation of an N-formyl-α-L-aspartyl-L-phenylalanine compound. An N-formyl-α-L-aspartyl-L-phenylalanine compound as meant herein is understood to be either N-formyl-α-L-aspartyl-L-phenylalanine or its methyl ester (F-α-AP or F-α-APM). The invention also relates to a method for preparation and recovery of α-APM from either (i) a mixture of N-formyl-α- and N-formyl-β-L-aspartyl-L-phenylalanine or (ii) a mixture of N-formyl-α- and N-formyl-β-L-aspartyl-L-phenylalanine methyl ester (F-αβ-AP or F-αβ-APM) by enzymatic deformylation. And finally, the invention relates to a simple method for one-pot enzymatic synthesis of α-APM from N-formyl-L-aspartic acid (F-Asp) and L- or D,L-phenylalanine methyl ester (L- or D,L-PM) also involving an enzymatic deformylation reaction. The latter combination of simultaneous enzymatic coupling and deformylation reactions has wider and more general applicability.

Aspartame (α-APM, L,L-form) is known to be a high intensity artificial sweetener, having a sweetness which is about 200× as potent as the sweetness of sucrose, whereas its tast properties are close to those of sucrose. The β-form of APM does not have sweet taste properties. α-APM is used for the sweetening of various edible materials. Synthesis methods for α-APM include chemical syntheses routes (e.g. by coupling of the anhydride of F-Asp with L-Phe or L-PM) which are invariably leading to mixtures of α- and β-forms of F-APM in ratios of about 70/30 to 80/20 wt./wt.). Apart from the required deformylation, these chemical methods therefore also require separation of the α-APM from β-APM and large recycle streams for recovery of α-APM in high purity and adequate yield. The synthesis methods for α-APM also include enzymatic coupling methods (e.g. by coupling of F-Asp or N-benzyloxy-carbonyl-L-Asp, also known as Z-Asp, with D,L-PM or L-PM). The enzymatic methods have the clear advantage that they selectively yield the α-coupled L,L-product in protected form. Although still needing a deprotection step, the enzymatic coupling routes therefore do not require difficult separation of α-APM from β-APM nor large recycle streams for recovery of α-APM in high purity and adequate yield. In the state of the art processes for the synthesis of α-APM many of those processes involve formyl-protection routes, and thus will need a deformylation step in one of the final stages of the process. Chemical deformylation, which is often performed in aqueous medium containing methanol and a strong acid, has the disadvantage that also demethylation of the phenylalanine methyl ester part of the molecule will occur, and mixtures of many compounds will be obtained in any subsequent methylation step. Enzymatic deformylation is believed to take place under mild conditions, and thus without simultaneous demethylation. However, so far no suitable enzymatic deformylation process seems to be available.

Enzymatic deformylation of an N-formyl-α-L-aspartyl-L-phenylalanine compound, namely of F-α-APM, is disclosed in Example 11 of U.S. Pat. No. 4,668,625. This patent teaches that penicillin-acylases are not suitable for removal of formyl-groups from oligopeptides. For instance, in Example 11 the yield is described to be 20% after 36 hours of reaction at an extremely high concentration of active enzyme as compared to the F-α-APM (namely 50 U of enzyme and 2 g of F-α-APM). However, even these results could not be reproduced by the present applicants. This is, amongst other things, because no clear disclosure is given of the Pseudomonas strain used and of the method of isolating the enzyme having penicillin-acylase activity therefrom.

Thus, there is need for an improved method of preparation for synthesis of α-L-aspartyl-L-phenylalanine methyl ester (α-APM; aspartame) involving enzymatic deformylation of an N-formyl-α-L-aspartyl-L-phenylalanine compound, without the disadvantages as mentioned above.

It now surprisingly has been found that enzymes having formylmethionyl peptide deformylase activity (hereinafter for convenience also represented by PDF or by PDF enzyme) can be used in the synthesis of aspartame. The method for synthesis of α-L-aspartyl-L-phenylalanine methyl ester by enzymatic deformylation of an N-formyl-α-L-aspartyl-L-phenylalanine compound according to the present invention comprises treating N-formyl-α-L-aspartyl-L-phenylalanine or its methyl ester with an enzyme having formylmethionyl peptide deformylase activity and having as a co-factor bivalent metal ions chosen from the group of group 5 to 11 metals from the periodic system of elements.

The periodic system of elements (new IUPAC version) and the group numbers as meant herein are presented in the Handbook of Chemistry and Physics, 70th edition, CRC Press, 1989–1990, inner page of cover. Bivalent metal ions from the group of group 5 to 11 metals are, for instance, $V^{2+}$, $Cr^{2+}$, $Mn^{2+}$, $Fe^{2+}$, $Co^{2+}$, $Ni^{2+}$, $Cu^{2+}$, $Pd^{2+}$, and $Pt^{2+}$. $Mn^{2+}$, $Fe^{2+}$, $Co^{2+}$ and $Ni^{2+}$ are preferred.

Preferably the amount of the bivalent metal ions should be about equivalent to the number of moles of enzyme. Suitably the molar ratio between these bivalent metal ions and the number of PDF molecules is in the range of 0.6 to 1.4, preferably of 0.8 to 1.2, and most preferred the amount of bivalent metal ions is equimolar to the enzyme.

In case F-α-AP is used as a starting material, of course, a final methylation step of the phenylalanine carboxylic acid group needs to be carried out in order to obtain the desired aspartame final product. Methods for such methylation are known to the skilled man, e.g. from U.S. Pat. No. 4,946,988 and EP-A-0468063.

Recovery of α-APM from the reaction mixture can be done by any method known to the skilled man. Various methods of crystallisation of aspartame have been described in the literature, e.g. in EP-A-0091787, EP-A-0399605 and EP-A-0582351. Preferably the recovery of α-APM is done at a pH near the iso-electric point of α-APM, i.e. at a pH in the range of 3 to 7.

The present invention is in particular surprising as there has not been any indication in the state of the art so far that PDF enzymes are also suitable for deformylating terminal N-formyl-L-aspartic acid residues in oligopeptides or dipeptides.

Enzymes having formylmethionyl peptide deformylase activity (PDF's) are widely available in nature. Mostly they are being described as formylmethionine deformylases. It should be noticed, however, that in the literature also other names are being used instead of the name formylmethionine deformylase; in particular the following names may be mentioned here: (poly)peptide deformylase, N-formylmethionylaminoacyl-tRNA deformylase, N-formyl-L-methionine amidohydrolase, N-formylmethionyl-aminoacyl-tRNA amidohydrolase.

The native PDF's in nature, e.g. in eubacteria, catalyse the deformylation of the formyl group from the terminal N-methionine residue in nascent polypeptides; more specifically, the PDF's catalyse the hydrolysis of the N-formyl group from the N-terminal L-methionine residue of nascent polypeptides synthesized by the ribosomal protein synthesis machinery. However, no other practical applications of these enzymes are known so far. On the contrary, Rajagopalan et al. (Biochem. 36, 13910-8 (1997)) have established that deformylases have strong sequence preference for methionine at the N-terminus of peptide substrates and to a lesser extent for norleucine at that site. It is thus surprising that these enzymes can be used favourably in the synthesis of α-APM.

The PDF's are obtainable, for instance, from eubacteria, for example *Escherichia coli, Bacillus subtilis, Clostridium beijerinckii, Clostridium acetobutylicum, Thermotoga maritima, Thermus aquaticus, Thermus thermophilus,* Calothrix PCC 7601, *Haemophilus influenzae, Bacillus stearothermophilus* or *Lactococcus lactis.* Preferably an enzyme from *Escherichia coli* is used.

The inventors have found that the PDF's in order to be able to be used in the synthesis methods according to the present invention require as a co-factor bivalent metal ions chosen from the group of group 5 to 11 metals from the periodic system of elements.

The reaction conditions for the enzymatic deformylation according to the invention are not very critical. Any suitable solvent system which is inert towards the PDF may be applied; such solvents include aqueous systems (solutions or slurries) or aqueous systems also containing a water-miscible organic solvent which is inert under the reaction conditions. Aqueous systems, however, are preferred. Also the concentration of the N-formyl compound is not critical, and may be for instance in the range of about 10 to 1000 mM. It is not necessary that all of the N-formyl compound is dissolved; part of it may be present as a slurry. The concentration of the PDF likewise is not very critical, and usually will be at 0.001 to 100%, normally less than 30.0% by weight of the formyl compound, e.g. at about 0.2 mM of PDF. The pH for the reaction preferably is chosen in the range of 3.0 to 9.0, more preferably of 4.0 to 8.0. The temperature is not very critical, and suitably will be in the range of 10 to 50° C., e.g. at about 37° C., but for thermostable PDF enzymes higher temperatures may be applied.

Until now a lot of work has been done with regard to the isolation and identification of PDF's. The following paragraphs give some more information on PDF's. Furtheron in this application, it will be made clear how PDF's having bivalent metal ions as required for the present invention can be obtained.

An example of a native PDF is the PDF-enzyme from *E. coli.* This has been shown to be a monomeric enzyme having a length of 168 amino acids with a molecular mass of 19197 Dalton as calculated from its amino acid sequence (minus the N-terminal methionine, which is removed by a post-translational modification step). This enzyme is made up of an active core domain composed of amino acids 1 to 147, and a C-terminal domain of amino acids 148–168; the latter domain, however, is not essential for the deformylase activity. The PDF coding gene from *E. coli* has been cloned (Mazel et al., EMBO J., 13, 914–923, (1994)) and very successful over-expression in *E. coli* of up to about $10^2$ to $10^3$ times of over-expression has been described using different expression constructs (Groche et al., (Biochem. and Biophys. Res. Comm., 246, 342–346 (1998)). Recently a comparison between the three-dimensional structures of the $Zn^{2+}$, $Fe^{2+}$ and $Ni^{2+}$ containing *E. coli* PDF's has been published (Becker et al., Nature Structural Biology, 5, 1998, 1053–1058).

Studies of PDF's, however, so far have been seriously hampered for a very long period of time because of the extreme lability of PDF's during purification, storage, and testing in dilute form. Based on the results of the biochemical characterisation studies with these extremely labile enzyme preparations, it was assumed until recently (e.g. see Meinnel et al., J. Mol. Biol., 262, 375–386, (1996)) that the native PDF enzyme from *E. coli* contains one $Zn^{2+}$ ion per enzyme molecule. The PDF's still are being considered to be a distinct family belonging to the zinc metalloprotease superfamily, but the $Zn^{2+}+$ ions are not suitable as a co-factor in the method of the present invention.

Recently it has been shown that PDF may be effectively stabilized during purification, storage and testing for formyl-methionyl peptide deformylase activity (in dilute form of the enzyme), by the addition of catalase. This and alternative stabilizing measures led to the further insight (see Rajagopalan, et al., J. Am. Chem. Soc., 119, 12418–12419 (1997), Becker et al., J. Biol. Chem., 273, 11413–6 (1998), Groche et al., (Biochem. and Biophys. Res. Comm., 246, 342–346 (1998), and Ragusa et al., (J. Mol. Biol., 280, 515–523 (1998)) that the presence of $Zn^{2+}$ in the earlier purified enzyme preparations from *E. coli* is mainly to be attributed to the isolation methods used, and that the $Zn^{2+}$ containing enzyme is (almost) completely catalytically inactive. The addition of catalase, and/or alternative stabilising measures, during the PDF purification procedure allows purification of the native, catalytically fully active *E. coli* PDF, which could be proven to contain one $Fe^{2+}$ ion per enzyme molecule instead of a $Zn^{2+}$ ion. It has been found that taking such stabilizing measures is also suitable during the methods for synthesis of α-APM according to the present invention.

One of the measures which are suitable for stabilizing the PDF is ensuring that the PDF's are being handled in an environment having reduced $O_2$ content, preferably under anaerobic conditions. Under such conditions almost no reduction of molecular oxygen to hydrogen peroxide takes place, with simultaneous oxidation of the bivalent metal ion, such as $Fe^{2+}$. Reduction of the content of dissolved $O_2$ can also be accomplished, by enzymatic removal of thereof, for instance by using a glucose oxidase/catalase system (Rajagopalan, P. T. R., and D. Pei, J. Biol. Chem., 273, No. 35, 22305–22310, (1998)). The presence of catalase prevents oxidation of the enzyme bound $Fe^{2+}$ to $Fe^{3+}$, which renders the PDF catalytically inactive. $Fe^{3+}$ is bound much more weakly than $Fe^{2+}$, and is therefore readily exchanged by $Zn^{2+}$ for which the metal ion binding site of the PDF has a much higher affinity. The net effect of such cascade of events is inactivation of the PDF.

Stabilisation of PDF's also can be achieved by alternative stabilising measures, namely by the addition/presence of other stabilisation agents, for instance of trialkylphosphine compounds or derivatives thereof; examples of such compounds are triethylphosphine, tributylphosphine and TCEP (tris-(2-carboxyethyl)-phosphine). Similarly as catalase, these stabilisation agents easily react with $H_2O_2$ or other peroxides. Further, inactivation of PDF's also can be prevented by handling the PDF's at higher concentration, for instance at a PDF concentration of at least 0.1 mg of PDF per ml, more preferably of at least 1.0 mg/ml. The upper limit of the concentration of PDF is not critical if practical concentrations are being used.

Exchange of the bivalent metal ions in the PDF's in order to obtain PDF enzymes with a co-factor as necessary for the present invention can be done by the various methods as described in Groche et al., Biochem. Biophys. Res. Comm., 246, 342–346, (1998). These methods include simple metal displacement by incubation of the native enzyme in an excess of the desired bivalent metal ion, if necessary preceeded by the preparation of the apoenzyme via treatment of the native enzyme with a metal chelation compound. Furthermore, the desired bivalent metal ion can already be introduced in (at least part of the enzyme molecules) by using a bacterial growth medium with an enhanced ratio of the desired bivalent metal ion over $Fe^{2+}$.

It is to be noticed that, instead of the enzymes used according to the method of the invention, of course, also whole cells, enzyme preparations, immobilised enzymes, etc. can be applied which are having formylmethionyl peptide deformylase activity. The terms enzyme, PDF, etc. as used herein, therefore also include such other forms of active enzyme, including genetically engineered mutants thereof, which for instance have enhanced activity or selectivity in the deformylation reaction.

The enzymes to be used can be classified according to standard classification schemes for enzyme activities. A very important group of enzymes having formylmethionyl peptide deformylase activity is classified as EC 3.5.1.27.

Preferably, the enzyme therefore is an enzyme having the activity as described for EC 3.5.1.27 because excellent results are being achieved in the deformylation with such enzymes. It should be noticed, although until recently it was believed that the enzyme coded as EC 3.5.1.31 is catalyzing a different reaction, but in the meantime it has been shown that the enzymes known as EC 3.5.1.27 and EC 3.5.1.31 are coded for by exactly the same gene and have the same activity. Therefore, as used herein, the term EC 3.5.1.27 is encompassing not only EC 3.5.1.31, but likewise all other enzymes having the same activity as described for EC 3.5.1.27.

Although the family of PDF's is composed of proteins with a relatively low level of sequence identity, the 3D structures of the members of this family appear closely related one to each other with, in particular, the building of a common fold around the bivalent metal ion and three signature sequences. As is described (for PDF's indicated as PDF) by Wagner et al., J. Biol. Chem., 273, 11413–6 (1998), for many of these enzymes characteristically three short amino acid stretches are present as strictly conserved motifs, namely in that the enzymes contain the sequences Ci) HEXXH, Cii) EGCLS (SEQ ID NO: 1) and (iii) GXGX-AAXQ (SEQ ID NO: 2). In these sequences X represents any natural amino acid, and standard one letter codes for amino acids are used: A=alanine, C=cysteine, E=glutamic acid, G=glycine, H=histidine, L=leucine, S=serine and Q=glutamine.

Preferably the method of the present invention is carried out using a PDF which is obtainable from *E. coli*.

In particular the co-factor bivalent metal ions in the PDF preferably are manganese, iron, cobalt and nickel ions. It has been indicated hereinbefore how such exchange of co-factor bivalent metal ions can be achieved.

Preferably in the method of the present invention PMdf's are being used which contain $Fe^{2+}$ and/or $Ni^{2+}$ ions in the active site because then highest activity and stability of the enzymes is observed. Especially preferred are PDF's which contain $Ni^{2+}$ ions, because those enzymes are much more resistent towards oxidation, and consequently more stable. As a consequence, the taking of stabilising actions and/or addition/presence of a stabilisation agent in such case is less important. Interestingly, the exchange of $Fe^{2+}$ for $Ni^{2+}$ does not significantly affect the enzyme's specific deformylating activity, which is at the same high level as with the $Fe^{2+}$ enzyme.

However, PDF's containing $Fe^{2+}$ ions (about one molar equivalent per molecule of enzyme) are most preferred, since they do not require metal exchange as compared to their native occurrence and because any remaining presence of the metal ions in the final product to be obtained is not likely to cause any problems, for instance toxicological problems. Of course, when isolating the enzyme and when using it in the course of the present invention, measures should be taken to avoid exchange of $Fe^{2+}$ by $Zn^{2+}$. Thus, preferably the bivalent metal ions are $Fe^{2+}$ ions and all treatments with the PDF enzyme are carried out in the presence of a stabilisation agent.

The term "in the presence of a stabilisation agent" as used here and hereinafter, is meant to include all measures shown above for the stabilisation of the PDF's.

Preferably the stabilisation agent is catalase or a trialkylphosphine compound or derivative, most preferably it is catalase.

In the course of inventors' studies on the use of the PDF's according to the invention in the synthesis of α-APM surprisingly a further advantage of such use has been found. In particular, it was observed that these enzymes are very regioselective. In particular they have a very high activity for deformylation of F-α-AP and F-α-APM, whereas they have no or only low activity for deformylation of F-β-AP or F-β-APM. Moreover, it has been found that presence of F-β-AP or F-β-APM does not give any inhibition of the PDF in the deformylation of F-α-AP and F-α-APM. These respective activities towards the α- and β-forms of F-AP and of F-APM now have been found to differ by at least a magnitude of 20× for F-AP, and by a magnitude of 200× or more for F-APM. Thus, in a preferred embodiment of the present invention an elegant and low-cost alternative is provided for the otherwise difficult separation of the α- and β-forms of AP and/or APM in α-APM production routes using formyl protection.

In this preferred embodiment of the invention the surprisingly found α-selectivity of the PDF enzymes according to the invention is used in selectively recovering α-APM from a mixture of F-α-APM and F-β-APM, or in selectively preparing α-AP from a mixture of F-α-AP and F-β-AP, followed by conversion of the α-AP into α-APM, and recovering the α-APM.

In this embodiment of the invention either (i) a mixture of N-formyl-α- and N-formyl-β-L-aspartyl-L-phenylalanine (F-αβ-AP) or (ii) a mixture of N-formyl-α- and N-formyl-β-L-aspartyl-L-phenylalanine methyl ester (F-αβ-APM) is treated with an enzyme having formylmethionyl peptide deformylase activity (PDF) and having as a co-factor bivalent metal ions chosen from the group of group 5 to 11 metals from the periodic system of elements, with the formation of α-L-aspartyl-L-phenylalanine or of its methyl ester, respectively, whereby in case α-L-aspartyl-L-phenylalanine (α-AP) is formed in the deformylation step a subsequent methylation step of the phenylalanine carboxylic acid group is carried out, and the α-L-aspartyl-L-phenylalanine methyl ester (α-APM) is recovered.

The subsequent methylation step, if applicable, and the recovery of α-APM are known to the skilled man, as has been described hereinabove.

The selective preparation of α-AP(M) from a mixture of F-α-AP(M) and F-β-AP(M) in particular can suitably be used in combination with chemical synthesis methods for AP(M) by formyl-protection routes. Until the present invention the formyl-deprotection step in such routes is troublesome and requires long reaction times and, usually, a further esterification step. Moreover, in such processes a mixture of at least eight compounds (four α-compounds: α-APM, α-AP, α-AMP and α-AMPM, and their corresponding β-compounds; in AMP the methyl ester group is present on the β-carboxyl function of the L-Asp moiety, and AMPM represents a dimethyl ester) is formed. Recovery of α-APM in these processes needs to be done through the intermediate selective precipitation and recovery of the α-APM.HCl salt, whereas the other seven compounds predominantly remain in solution and need to be recycled and reconverted into their starting materials L-Asp and L-Phe (by hydrolysis) and, after recovery thereof, again into α-APM. This is disadvantageous because of the very long reaction times, relatively low once-through yield of α-APM and low efficiency on L-Asp and L-Phe due to losses in the recovery.

Preferably, in this second embodiment of the invention, the PDF is an EC 3.5.1.27 enzyme because then excellent results are being achieved. More preferably, the PDF contains the sequences i) HEXXH, (ii) EGCLS (SEQ ID NO: 1) and (iii) GXGXAAXQ (SEQ ID NO: 2). In particular the PDF used is obtainable from E. coil, and the bivalent metal ions are manganese, iron, cobalt and nickel ions. It is even more preferred that the bivalent metal ions are iron and/or nickel ions. Preferably the bivalent metal ion is $Fe^2$ and all the treatments with the PDF enzyme are carried out in the presence of a stabilisation agent. In that case the stabilisation agent is preferably catalase or a trialkylphosphine compound or derivative, and most advantageously it is catalase.

For all further relevant remarks as to reaction conditions etc. reference is made to the details given above in discussing the first embodiment of the invention.

In another preferred embodiment of the invention the enzymatic deformylation step according to the invention is integrated into a novel one-pot enzymatic synthesis of α-APM. In particular, in such embodiment N-formyl-L-aspartic acid (F-Asp) is coupled enzymatically, using thermolysin as the coupling enzyme, with L- or D,L-phenylalanine methyl ester (L- or D,L-PM), and simultaneously, and in the same reaction vessel, the N-formyl-α-L-aspartyl-L-phenylalanine methyl ester (N-F-α-APM) formed by the coupling reaction is deformylated by an enzyme having formylmethionyl peptide deformylase activity (PDF) and having as a co-factor bivalent metal ions chosen from the group of group 5 to 11 metals from the periodic system of elements and being present in the reaction system for the enzymatic coupling reaction.

It is noticed that the term "thermolysin" as used here and hereinafter is intended to mean thermolysin, including any mutant thereof, and any other enzyme which has suitable coupling activity for said enzymatic coupling reaction.

Preferably, the α-APM so formed is recovered after the reaction has proceeded till a conversion of more than 40%. Conversion as meant here relates to the conversion of the L-PM starting in the coupling step to the desired α-APM endproduct. Without the simultaneous deformylating step the yield of the enzymatic coupling reaction of F-Asp and L- or D,L-PM (which is thermodynamically unfavourable due to the position of the equilibrium of this reaction) is lying strongly on the side of the substrates. Simultaneous presence of a PDF during the coupling reaction results in a favourable shift to the right side thereof, thereby directly leading to α-APM. In contrast, if no PDF is used according to the present invention, troublesome other measures need to be taken to shift said equilibrium and it is impossible to synthesize the α-APM in a direct one-pot production method. In the absence of the PDF direct yield of α-APM is zero. Attempts to shift the equilibrium more favourably to the side of synthesis (of F-α-APM, not of α-APM) already have been made by creating reaction conditions where the F-α-APM formed is precipitated in situ as an addition compound with L- or D-PM. However, such formation of an addition compound requires relatively high concentrations (and excess, 2 equivalents) of L-PM or D,L-PM. In the latter case intermediate precipitation of a F-α-APM adduct with L- and/or D-PM will occur (and in the former case of the F-α-APM.L-PM addition compound). Therefore, surprisingly, according to this third embodiment of the present invention conversion with direct formation of α-APM has become possible.

This advantageous third embodiment of the present invention is only possible due to the surprising finding that the PDF's as used herein do not have very significant deformylating activity towards F-Asp as compared to their deformylating activity towards the N-formyl-α-dipeptide derivatives or other (N-terminal) N-formyl oligopeptides.

This is the more surprising as it is well known to the skilled man that for most other deprotecting enzymes known in peptide chemistry (e.g. PenG-acylases for the removal of phenylacetic acid residues, or decarbamoylase enzymes for the removal of carbamoyl groups) no such significant differences in activity towards the protected monomeric and oligomeric compounds are being found. On the contrary, the difference in activity towards the protected monomeric and oligomeric compounds is either almost absent (e.g. for PenG-acylases) or opposite, i.e. there is much higher activity for the protected monomeric compound (e.g. for decarbamoylases).

It is thus completely unexpected that the PDF's as used according to the present invention would be suitable in the methods of the present invention. The PDF's as used in the methods of the present invention behave completely different from other deacylating enzymes (or amidohydrolases).

This embodiment of the present invention is in particular surprising as there has not been any indication in the state of the art so far that PDF enzymes are suitable for deformylating terminal N-formyl-L-aspartic acid residues in oligopeptides or dipeptides. Moreover, the PDF's have significantly different deformylating activities towards N-formyl amino acids and towards (N-terminal) N-formyl oligopeptides. This enables a technically feasible process with precipitation of α-APM without substantial formation of by-products (e.g. of the diketopiperazine of α-APM), and without need for large recycles, etc., in a one-pot single-step process.

The reaction conditions for this third embodiment of the present invention again are not very critical. As already mentioned above for the first embodiment thereof, any suitable solvent system which is inert towards the PDF may be applied; such solvents include aqueous systems (solutions or slurries) or aqueous systems also containing a water-miscible organic solvent which is inert under the reaction conditions. Aqueous systems, however, are preferred. Also the concentration of the N-formyl starting compound (F-Asp) is not critical, and may be for instance in the range of about 10 to 1000 mM. It is not necessary that all of the N-formyl compound is dissolved; part of it may be present as a slurry. The concentration of the PDF likewise is not very critical, and usually will be at 0.001 to 100.0%, normally less than 30%, by weight of the formyl compound, e.g. at about 0.2 mM of PDF. The pH for the reaction preferably is chosen in the range of 3.0 to 9.0, more preferably of 4.0 to 8.0 because then α-APM is formed without any significant formation of by-products and the enzymes used are being maintained at high stability and activity. If the α-APM formed is precipitated there is even less risk for by-product formation. The temperature is not very critical, and suitably will be in the range of 10 to 50° C., e.g. at about 37° C., but for thermostable PDF enzymes higher temperatures may be applied.

In this third embodiment of the invention good results are obtained if the PDF is an enzyme having the activity as described for EC 3.5.1.27. Preferably, the PDF enzyme contains the sequences of i) HEXXH, (ii) EGCLS (SEQ ID NO: 1) and (iii) GXGXAAXQ (SEQ ID NO: 2)

It is particularly advantageous in this third embodiment of the invention, if the PDF enzyme has a deformylating activity towards (oligo)peptides with N-formylmethionine at their N-terminus, which is at least 10× higher, preferably at least 100× higher, and most preferred at least 200× higher than its deformylating activity towards N-formyl methionine.

It is to be noticed that the deformylation activity of the PDF's, in order to select most suitable PDF's, also may be determined for (N-terminal) N-formyl compounds other than the N-formylmethionine (oligo)peptides and their corresponding N-formyl amino acids. The ratio between the deformylating activity values obtained for such other N-formyl (oligo)peptides and amino acids can be taken as an approximate measure for the suitability of the specific PDF in this third embodiment.

This preferred embodiment of the invention may even have more general applicability than for the synthesis of α-APM. It is particularly advantageous when the enzymatic deformylation reaction is simultaneously carried out with the enzymatic coupling of an N-formyl amino acid (in the case of α-APM synthesis this is F-Asp) and another amino acid or (oligo)peptide which is unprotected at the terminal amino group (in the case of α-APM synthesis this is L-PM).

Preferably, the method of the present invention is carried out using a PDF which is obtainable from *E. coli*. In particular the co-factor bivalent metal ions in the PDF preferably are $Mn^{2+}$, $Fe^{2+}$, $Co^{2+}$ and $Ni^{2+}$ ions. It has been indicated hereinbefore how such exchange of co-factor bivalent metal ions can be achieved.

Preferably in this embodiment of the present invention PDF's are being used which contain $Fe^{2+}$ and/or $Ni^{2+}$ ions in the active site.

In particular, the bivalent metal ions are $Fe^{2+}$ ions and all treatments with the PDF enzyme are carried out in the presence of a stabilisation agent. Preferably the stabilisation agent is catalase or a trialkylphosphine compound or derivative, most preferably it is catalase.

In addition to all abovementioned remarks as to reaction conditions etc. it should be noticed that in this third embodiment of the invention, in order to maintain the activity of both the thermolysin coupling enzyme (which is an endoproteinase) and the PDF at a sufficiently high level, taking one or more additional measures may lead to better results. For instance, it may be advisable to prevent any potential proteolytic degradation of the PDF used by thermolysin. In particular, it can be advantageous to use the thermolysin and/or the PDF in immobilized form. Immobilization may be taken care of by any method available to the skilled man. A suitable method is using the enzymes in the form of so-called CLEC's ("cross-linked enzyme crystals"). Other methods include use of so-called "crystalline enzyme" thermolysin and PDF.

Alternatively, genetically engineered mutants of PDF's may be used which have (a still acceptable, preferably unaltered or even enhanced) activity towards the deformylation reaction but are less prone to deactivation in the presence of thermolysin. These mutants can be generated by a number of different approaches; for instance, by site-directed mutagenesis, site-specific random mutagenesis, regio-specific random mutagenesis, and completely random mutagenesis; the latter form of mutagenesis is better known as directed evolution. General applicable methods to perform these different protein engineering approaches are well known to the skilled man. If a random approach will be applied, the mutagenesis cycle will need to be followed by selection of resistent and active mutant(s), thereby leading to the identification of suitable mutants that no longer contain the thermolysin accessible sites. To obtain PDF mutants, which are completely resistent to thermolysin degradation, a combination of different protein engineering approaches and/or several rounds of random mutagenesis appears to be the most effective procedure.

Vice versa mutants of thermolysin can be made having (a still acceptable, but preferably unaltered or even enhanced) coupling activity, but giving less inactivation of the PDF's.

Another suitable method for avoiding mutual deactivation of the thermolysin and the PDF is the use of a physical barrier between both enzymes, which prevents that both enzymes come into direct contact while allowing almost unhindered transport of reactants and products. An example of a suitable physical barrier are dialysis membranes with a cut-off value of about 10 kDa, where the thermolysin is present at one side of the membrane as well as part of the substrates for the coupling reaction, and where the PDF and part of the reaction products are present at the other side thereof.

As a result of the above investigations regarding the suitable one-pot enzymatic process for the synthesis of α-APM, the inventors have found that the concept of such one-pot process, i.e. a combination of an enzymatic coupling reaction and simultaneous deformylation of the coupling product, has wider and more general applicability than for the synthesis of α-APM alone.

In its broadest scope the present invention therefore also relates to novel one-pot syntheses of di- or oligopeptides or derivatives thereof from two starting materials, the first of which is an N-formyl protected amino acid which is capable of undergoing an enzymatic coupling reaction with a second amino acid or derivative thereof, or with a di- or oligo-peptide or derivative thereof, thereby yielding an N-formyl protected reaction compound, wherein the N-formyl protecting group of the first starting material is retained during the enzymatic coupling reaction with the second starting material, whereby said protecting group is cleaved off enzymatically, using an enzyme having formylmethionyl peptide deformylase activity and having as a co-factor bivalent metal ions chosen from the group of group 5 to 11 metals from the periodic system of elements, from the reaction compound at a substantially higher, i.e. at least 10× higher, rate than from the first starting material, and wherein two enzymes are involved simultaneously for the enzymatic coupling reaction between the starting materials and the enzymatic deformylation of the reaction compound.

Examples of such combinations of enzymes, starting materials (and protecting groups thereof), and final products are shown in table 1 below:

TABLE 1

| Starting materials | Enzymes | Final product |
| --- | --- | --- |
| A1. N-Formyl-L-valine<br>A2. L-Phenylalanine methyl ester | Aa. Thermolysin<br>Ab. PDF | L-Valinyl-L-phenylalanine methyl ester |
| B1. N-Formyl-L-aspartic acid<br>B2. L-Phenylalanyl-L-phenylalanine methyl ester | Ba. Thermolysin<br>Bb. PDF | L-Aspartyl-L-phenylalanyl-L-phenylalanine methyl ester |
| C1. N-Formyl-L-aspartic acid<br>C2. L-Phenylalanine methyl ester | Ca. Papain<br>Cb. PDF | α-APM |
| D1. N-Formyl-L-aspartic acid<br>D2. L-Phenylalanine amide | Da. Thermolysin<br>Db. PDP | L-Aspartyl-L-phenyl-alanyl amide |

The invention will now be illustrated by means of the following Examples and Comparative Examples. However, the scope of the present invention is by no means restricted by the Examples shown.

Isolation of PDF ($Fe^{2+}$)

For a detailed discussion of the methods used reference is made to Groche et al., BBRC 246, 342–346 (1998). The following paragraph gives a summary thereof; abbreviations are explained below.

An EC 3.5.1.27 PDF ($Fe^{2+}$) enzyme was isolated from overproducing *E. coli* cells grown at 30° C. in 1.6 l TB medium for 14–16 hours. About 13 g (wet weight) of cell paste were suspended in 26 ml buffer (20 mM Hepes/KOH, 100 mM KF, pH 7.7 supplemented with 10 μg/ml catalase from bovine liver (Boehringer Mannheim) and 1 mM AEBSF, disintegrated by sonification (Branson B12, 20 min) at 0° C. and centrifuged at 200.000 g for 1 hour. The clear supernatant (1.3 g of protein; according to biurete reaction) was mixed with 1.3 ml 10% (w/v) Polymin G-35 (BASF) adjusted to pH 7.7 and centrifuged at 40.000 g for 10 minutes. The supernatant was applied to a 20 ml Met-Lys-Sepharose column that had been equilibrated with 20 mM Hepes/KOH, 100 mM KF, 0.2 mM TCEP, pH 7.7. After washing with 120 ml of 20 mM Hepes/KOH, 100 mM KF, 0.2 mM TCEP, pH 7.7, the PDF ($Fe^{2+}$) was eluted with 150 ml 20 mM Hepes/KOH, 100 mM KCl, 0.2 mM TCEP, pH 7.7. The protein containing fractions were concentrated by ultrafiltration using an Amicon PM10 membrane (yield: 140 mg protein, having an activity of 800 IU/mg; assay conditions: 5 mM formylmethionyl-alanine, 30° C., pH=7.2). After adjustment of the TCEP concentration to 1 mM and protein concentration to 40 mg/ml PDF ($Fe^{2+}$) was stored frozen at −60° C.

TB medium: 12 g/l of Bacto-Tryptone, Difco; 24 g/l of yeast extract, Difco; 4 g/l of glycerole; 2.3 g/l of $KH_2PO_4$; 12.5 g/l of $K_2HPO_4$)

Hepes: N-2-hydroxyethylpiperazine-N'-2-ethane sulphuric acid;

AEBSF: 2-aminoethyl-p-benzene sulphonyl fluoride;

TCEP: tris-(2-carboxyethyl)-phosphine.

HPLC Analysis of the Starting Materials and Reaction Products

Analysis of all compounds was carried out with a reversed-phase HPLC column (Nucleosil 300-5 $C_{18}$ 4.6 mm×250 mm; Macherey-Nagel, Düren) using a linear gradient (within 30 minutes) of 0 to 24% (vol/vol) acetonitrile in aqueous 0.1% (vol/vol) trifluoro-acetic acid at a flow rate of 1 ml/min and at ambient temperature. All compounds were detected by UV-spectrophotometry at a wavelength of 254 nm.

Deformylation Reactions

Deformylation reactions (Examples 1–3, and Comparative Examples A–C) were performed as follows:

Compounds (100 mM) as indicated in Table 2 for each separate Example were incubated in the presence of 100 mM aqueous 2-(N-morpholino)-ethanesulphonic acid (MES)/KOH buffer pH=6.2 and 250 mM KCl at 37° C. The reactions of the Examples and Comparative Examples A–C were started by the addition of PDF ($Fe^{2+}$), as prepared above, to a final concentration of 0.2 mM. At various times samples (5 μl) were withdrawn and mixed with 45 μl of aqueous $HClO_4$ (2% vol/vol final concentration) to terminate the reaction in order to be able to measure concentrations of deformylated compounds (containing a free amino group). Following a brief centrifugation, the amount of deformylated compounds in the supernatant was determined by trinitrobenzene sulphonic acid (TNBS) according to the method of Fields (Methods in Enzymology, 25, 464–468 (1972)), using $\epsilon_{420}=21.2$ $mM^{-1}$ $cm^{-1}$. The amount of (deformylated) compound each time was corrected for the intrinsic amount of free amino compound which was detected without incubation with the PDF. Identification of the reaction compounds was also confirmed by HPLC analysis (as described above).

The results are summarized in table 2. The product yields indicated are the yields after 10 hours of reaction time. It has been shown in case of Examples 1 and 2 that the deformylation reactions can be continued to a conversion of more than 90%.

In addition, the catalytic properties of the PDF in the deformylation reactions of F-α-AP and F-α-APM (in particular the initial reaction rates for deformylation in resp. 1 hour for F-α-APM and 3 hours for F-α-AP) were determined by performing the reactions of Examples 1 and 2 at various substrate concentrations from 2–140 mM. In particular, the following catalytic properties of the enzyme were determined:

| | | |
| --- | --- | --- |
| $K_M$ | [mM] : | Michaelis constant (this is the substrate concentration at which the reaction rate is 50% of the maximum reaction rate observed) |
| $k_{cat}$ | $[min^{-1}]$ : | turnover number |
| $k_{cat}/K_M$ | $[M^{-1}sec^{-1}]$ : | catalytic efficiency (also called: specificity constant) |

The values determined are also given in table 2.

The following Examples and Comparative Examples were performed:

EXAMPLE 1

Use of PDF ($Fe^{2+}$) for synthesis of α-APM from F-α-APM

EXAMPLE 2

Use of PDF ($Fe^{2+}$) for synthesis of α-AP from F-α-AP

EXAMPLE 3

Use of PDF ($Fe^{2+}$) for synthesis of α-APM from F-αβ-APM (Note: 100 mM F-α-APM, 25 mM F-β-APM)

Comparative Example A

Use of PDF ($Fe^{2+}$) for deformylation of F-β-APM

Comparative Example B

Use of PDF ($Fe^{2+}$) for deformylation of F-β-AP

Comparative Example C

Use of PDF ($Fe^{2+}$) for deformylation of F-Asp

TABLE 2

Enzyme: PDF($Fe^{2+}$)

| Example or Comp. Example | substrate | product | yield (%) | $K_M$ [mM] | $k_{cat}$ [$min^{-1}$] | $k_{cat}/K_M$ [$M^{-1}sec^{-1}$] |
|---|---|---|---|---|---|---|
| 1 | F-α-APM | α-APM | 44.2 | 25.3 | 0.7 | 0.46 |
| 2 | F-α-AP | α-AP | 21.6 | 12.3 | 0.2 | 0.27 |
| 3 *) | F-αβ-APM | α-APM | 44 | | | 0.46 |
|  |  | β-APM | <0.1 | | | <0.0001 |
| A | F-β-APM | β-APM | 0.2 | | | <0.0001 |
| B | F-β-AP | β-AP | 1.1 | | | <0.0001 |
| C | F-Asp | Asp | 0.5 | | | |

*) In this example no inhibition by F-β-APM of the enzyme activity towards F-α-APM was observed.

Comparative Example D use of penicillin-acylase for synthesis of α-APM from F-α-APM.

This experiment was performed, slightly different from the Examples described above, as follows:

1 g of F-α-APM was dissolved in 25 ml of distilled water and the pH was adjusted to 6,5 by the addition of 0.1 M aqueous NaOH. Then, 0.2 g of an immobilized penicillin-acylase preparation was added. The reaction mixture was allowed to stand for 48 hours at 37° C. At regular time intervals during the reaction, samples were taken and analyzed by thin layer chromatography using α-APM as a reference substance. In none of the samples taken, formation of α-APM from F-α-APM could be demonstrated.

EXAMPLE 4

One-pot Enzymatic Synthesis of α-APM from F-Asp and L-PM.

5 mg/ml of CLEC-thermolysin (PeptiCLEC-TR, from Altus Biologics Inc., Cambridge, USA) was stirred at room temperature in a buffer solution containing 100 mM MES/KOH (pH=6.2), 1.7 M NaCl, 10 mM $CaCl_2$, 1 M of F-Asp and 100 mM of L-PM. The coupling reaction started and continued for about 3–4 hours until a level of the F-α-APM concentration was reached of about 11 mM. Then 8 mg/ml of PDF ($Fe^{2+}$) as prepared above were added to the reaction mixture and the reaction was continued for 20 more hours. During said period the concentration of the F-α-APM decreased to about 7 mM, whereas gradually formation of 19 mM of α-APM was observed. At 24 hours the amount of L-PM was 55 mM and of L-Phe formed 18 mM; at that time also 3 mM of the diketopiperazine of α-APM was present. It is thus demonstrated that the equilibrium of the coupling reaction is shifted to the right side by the treatment with PDF ($Fe^{2+}$) and that simultaneously α-APM is formed in this one-pot process. It has been shown, moreover, that the reaction is still proceeding after said 24 hours; thus, higher yields of α-APM can be achieved.

---

What is claimed is:

1. Method for synthesis of α-L-aspartyl-L-phenylalanine methyl ester by enzymatic deformylation of an N-formyl-α-L-aspartyl-L-phenylalanine compound, characterized in that N-formyl-α-L-aspartyl-L-phenylalanine or its methyl ester is treated with an enzyme having formylmethionyl peptide deformylase activity and having as a co-factor bivalent metal ions chosen from the group of group 5 to 11 metals from the periodic system of elements.

2. Method according to claim 1, characterized in that the enzyme having formylmethionyl peptide deformylase activity is an enzyme having the activity as described for EC 3.5.1.27.

3. Method according to any of claims 1 or 2, characterized in that the enzyme having formylmethionyl peptide deformylase activity contains the sequences of
 (i) HEXXH,
 (ii) EGCLS (SEQ ID NO: 1) and
 (iii) GXGXAAXQ (SEQ ID NO: 2).

4. Method according to any of claim 1, characterized in that the enzyme having formylmethionyl peptide deformylase activity is obtainable from *E. coli*.

5. Method according to claim 1, characterized in that the bivalent metal ions are manganese, iron, cobalt and nickel ions.

6. Method according to claim 5, characterized in that the bivalent metal ions are iron and/or nickel ions.

7. Method according to claim 6, characterized in that the bivalent metal ions are iron ions and all treatments with the enzyme having formylmethionyl peptide deformylase activity are carried out in the presence of a stabilisation agent.

8. Method according to claim 7, characterized in that the stabilisation agent is catalase or a trialkylphosphine compound or derivative.

9. Method according to claim 8, characterized in that the stabilisation agent is catalase.

10. Method for the preparation and recovery of α-L-aspartyl-L-phenylalanine methyl ester by enzymatic deformylation of an N-formyl-α-L-aspartyl-L-phenylalanine compound, characterized in that either
 (i) a mixture of N-formyl-α- and N-formyl-β-L-aspartyl-L-phenylalanine or
 (ii) a mixture of N-formyl-α- and N-formyl-β-L-aspartyl-L-phenylalanine methyl ester is treated with an enzyme having formylmethionyl peptide deformylase activity and having as a co-factor bivalent metal ions chosen from the group of group 5 to 11 metals from the periodic system of elements, with the formation of α-L-aspartyl-L-phenylalanine or of its methyl ester, respectively, whereby in case α-L-aspartyl-L-phenylalanine is formed in the deformylation step a subsequent methylation step of the phenylalanine carboxylic acid group is carried out, and the α-L-aspartyl-L-phenylalanine methyl ester is recovered.

11. Method according to claim 10, characterized in that the enzyme having formylmethionyl peptide deformylase activity is an enzyme having the activity as described for EC 3.5.1.27.

12. Method according to any of claims 10 or 11, characterized in that the enzyme having formylmethionyl peptide deformylase activity contains the sequences of
 (i) HEXXH,
 (ii) EGCLS (SEQ ID NO: 1) and
 (iii) GXGXAAXQ (SEQ ID NO: 2).

13. Method according to claim 10, characterized in that the enzyme having formylmethionyl peptide deformylase activity is obtainable from *E. coli*.

14. Method according to claim 10, characterized in that the bivalent metal ions are manganese, iron, cobalt and nickel ions.

15. Method according to claim 14, characterized in that the bivalent metal ions are iron and/or nickel ions.

16. Method according to claim 15, characterized in that the bivalent metal ions are iron ions and all the treatments with the enzyme having formylmethionyl peptide deformylase activity are carried out in the presence of a stabilisation agent.

17. Method according to claim 16, characterized in that the stabilisation agent is catalase or a trialkylphosphine compound or derivative.

18. Method according to claim 17, characterized in that the stabilisation agent is catalase.

19. Method for synthesis of α-L-aspartyl-L-phenylalanine methyl ester by enzymatic deformylation of an N-formyl-α-L-aspartyl-L-phenylalanine compound, characterized in that N-formyl-L-aspartic acid is coupled enzymatically, using thermolysin as the coupling enzyme, with L- or D,L-phenylalanine methyl ester, and that simultaneously, and in the same reaction vessel, the N-formyl-α-L-aspartyl-L-phenylalanine methyl ester formed by the coupling reaction is deformylated by an enzyme having formylmethionyl peptide deformylase activity and having as a co-factor bivalent metal ions chosen from the group of group 5 to 11 metals from the periodic system of elements and being present in the reaction system for the enzymatic coupling reaction.

20. Method according to claim 19, characterized in that, the α-APM so formed is recovered after the reaction has proceeded till a conversion of more than 40%.

21. Method according to claim 19, characterized in that the enzyme having formylmethionyl peptide deformylase activity is an enzyme having the activity as described for EC 3.5.1.27.

22. Method according to any of claims 19–21, characterized in that the enzyme having formylmethionyl peptide deformylase activity contains the sequences of
 (i) HEXXH,
 (ii) EGCLS (SEQ ID NO: 1) and
 (iii) GXGXAAXQ (SEQ ID NO: 2).

23. Method according to claim 19, wherein the enzyme having formylmethionyl peptide deformylase activity has a deformylating activity towards (oligo) peptides with N-formylmethionine at their N-terminum, which is at least 10× higher than its deformylating activity towards N-formyl methionine.

24. Method according to claim 19, characterized in that the enzyme having formylmethionyl peptide deformylase activity is obtainable from *E. coli*.

25. Method according to claim 19, characterized in that the bivalent metal ions are manganese, iron, cobalt and nickel ions.

26. Method according to claim 25, characterized in that the bivalent metal ions are iron and/or nickel ions.

27. Method according to claim 26, characterized in that the bivalent metal ions are iron ions and all treatments with the enzyme having formylmethionyl peptidedeformylase activity are carried out in the presence of a stabilisation agent.

28. Method according to claim 27, characterized in that the stabilisation agent is catalase or a trialkylphosphine compound or derivative.

29. Method according to claim 28, characterized in that the stabilisation agent is catalase.

30. Method according to claim 19, wherein the enzyme having formylmethionyl peptide deformylase activity has a deformylating activity towards (oligo) peptides with N-formylmethionine at their N-terminum, which is at least 100× higher than its deformylating activity towards N-formyl methionine.

31. Method according to claim 19, wherein the enzyme having formylmethionyl peptide deformylase activity has a deformylating activity towards (oligo) peptides with N-formylmethionine at their N-terminum, which is at least 200× higher than its deformylating activity towards N-formyl methionine.

* * * * *